US00RE39127E

(19) United States
(12) Reissued Patent
Shiokawa et al.

(10) Patent Number: US RE39,127 E
(45) Date of Reissued Patent: Jun. 13, 2006

(54) HETEROCYCLIC COMPOUNDS

(75) Inventors: Kozo Shiokawa, Kanagawa-ken (JP); Shinichi Tsuboi, Tokyo (JP); Shinzo Kagabu, Gifu-ken (JP); Shoko Sasaki, Tokyo (JP); Koichi Moriya, Tokyo (JP); Yumi Hatori, Tokyo (JP)

(73) Assignee: Bayer Cropscience K.K., Tokyo (JP)

(21) Appl. No.: 10/067,191

(22) Filed: Feb. 4, 2002

Related U.S. Patent Documents

Reissue of:
(64) Patent No.: 4,849,432
Issued: Jul. 18, 1989
Appl. No.: 07/017,641
Filed: Feb. 24, 1987

(30) Foreign Application Priority Data

Mar. 7, 1986 (JP) ..... 61-48629

(51) Int. Cl.
*A61K 31/44* (2006.01)
*A61K 31/4439* (2006.01)
*A61K 31/506* (2006.01)
*C07D 401/06* (2006.01)
*C07D 417/06* (2006.01)

(52) U.S. Cl. ..... 514/256; 514/333; 514/340; 514/341; 514/342; 544/55; 544/96; 544/238; 544/242; 544/333; 544/334; 544/336; 544/409; 546/256; 546/270.7; 546/271.4; 546/274.7; 546/279.1; 548/127; 548/131; 548/134; 548/136; 548/143; 548/146; 548/193; 548/214

(58) Field of Classification Search ..... 544/333; 514/256
See application file for complete search history.

(56) References Cited

U.S. PATENT DOCUMENTS

| | | | | |
|---|---|---|---|---|
| 4,247,705 | A | 1/1981 | Cale, Jr. | 548/315 |
| 4,468,518 | A | 8/1984 | Fujimoto et al. | 548/342 |
| 4,616,025 | A | 10/1986 | Ezer et al. | 514/342 |
| 4,647,570 | A | 3/1987 | Shiokawa et al. | 514/341 |
| 4,678,795 | A | 7/1987 | Shiokawa et al. | 514/341 |
| 4,680,294 | A | 7/1987 | Shiokawa et al. | 514/256 |
| 4,880,933 | A | 11/1989 | Shiokawa et al. | 544/332 |
| 4,914,113 | A | 4/1990 | Shiokawa et al. | 544/333 |
| 4,948,798 | A | 8/1990 | Gsell | 514/275 |
| 4,988,712 | A | 1/1991 | Shiokawa et al. | 514/340 |
| 5,063,236 | A | 11/1991 | Gsell | 514/318 |
| 5,308,855 | A | 5/1994 | Tsuboi et al. | 514/341 |

FOREIGN PATENT DOCUMENTS

| | | | |
|---|---|---|---|
| DE | 2 205 745 | | 8/1973 |
| DE | 3 409 801 | | 9/1984 |
| FR | 2 542 740 | | 9/1984 |
| GB | 2 126 220 | | 3/1984 |
| GB | 2126222 | * | 3/1984 |
| JP | 59-196877 | | 11/1987 |

OTHER PUBLICATIONS

Patent Abstracts of Japan, vol. 9, No. 241 (C–306), (1964) Sep. 27, 1985.
Patent Abstracts of Japan, vol. 8, No. 122 (C–227), (1959) Jun. 8, 1984.
Tsuboi, Chem. Abstr., vol. 109, entry 144610r (1988).
Tsuboi, Chem. Abstr., vol. 109, entry 144611s (1988).

* cited by examiner

*Primary Examiner*—Richard L. Raymond
(74) *Attorney, Agent, or Firm*—Norris McLaughlin & Marcus, P.A.

(57) ABSTRACT

Novel heterocyclic compounds of the formula (I)

wherein, $R^1$ represents a hydrogen atom or an alkyl group, A represents an ethylene group which may be substituted by alkyl or a trimethylene group which may be substituted by alkyl, X represents an oxygen or sulfur atom or the group in which $R^2$ represents a hydrogen atom of an optionally substituted alkyl, an alkenyl, an alkynyl or an acyl group, and $R^3$ represents a hydrogen atom or an alkyl group, and Z represents an optionally sibstituted 5- or 6-membered heterocyclic group which contains at least two hetero atoms selected from oxygen, sulfur and nitrogen atoms, or an optionally substituted 3- or 4-pyridyl group.

The above defined novel heterocyclic compounds of formula (I) exhibit powerful insecticidal properties.

1 Claim, No Drawings

HETEROCYCLIC COMPOUNDS

Matter enclosed in heavy brackets [ ] appears in the original patent but forms no part of this reissue specification; matter printed in italics indicates the additions made by reissue.

*This application is a reissue of U.S. Pat. No. 4,849,432, issued on Jul. 18, 1989. Another pending reissue application related to the same patent is U.S. Ser. No. 08/254,202, filed Jun. 6, 1994.*

*Notice: More than one reissue application has been filed for the reissue of U.S. Pat. No. 4,849,432. The reissue applications are application Nos. 08/254,202 (the present application), filed on Jun. 6, 1994; 10/067,189, filed on Feb. 4, 2002; 10/067,190, filed on Feb. 4, 2002; 10/067,191 filed on Feb. 4, 2002; and 10/167,192, filed on Feb. 4, 2002; all of which are divisional reissues of U.S. Pat. No. 4,849,432.*

The present invention relates to novel heterocyclic compounds, to processes for their preparation, and to their use as insecticides.

It has already been disclosed that certain cyanoimino-substituted heterocyclic compounds are useful as intermediates for fungicidal, antidiabetic, viral tranquilizing or diuretic active substances (see DE-OS No. 2,205,745) and also as antiulcer agents (see DE-OS No. 3,409,801).

There have now been found novel heterocyclic compounds of the formula (I)

(I)

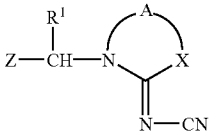

wherein, $R^1$ represents a hydrogen atom or an alkyl group, A represents an ethylene group which may be substituted by alkyl or a trimethylene group which may be substituted by alkyl, X represents an oxygen or sulfur atom or the group

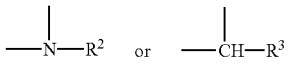

in which $R^2$ represents a hydrogen atom or an optionally substituted alkyl, alkenyl, alkynyl or acyl group, and $R^3$ represents a hydrogen atom or an alkyl group, and Z represents an optionally substituted 5- or 6-membered heterocyclic group which contains at least two hetero atoms selected from oxygen, sulfur and nitrogen atoms, or an optionally substituted 3- or 4-pyridyl group.

The compounds of the formula (I) are obtained by a process in which (a) compounds of the formula (II)

(II)

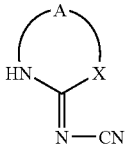

wherein A and X are as defined, are reacted with compounds of the formula (III)

(III)

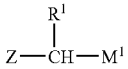

wherein $R^1$ and Z are as defined above, and $M^1$ represents a halogen atom or the group $—OSO_2—M^2$ in which $M^2$ represents a lower alkyl group or an aryl group, in the presence of inert solvent, if appropriate in the presence of a base, or (b) in the case where X in the formula (I) represents an oxygen or sulfur atom or the group

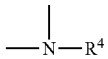

in which $R^4$ represents a hydrogen atom, an alkyl group which may be substituted, an alkenyl group or an alkynyl group, and for which case in the following formula (IV) X is replaced by the symbol $X^1$: Compounds of the formula (IV)

(IV)

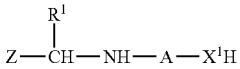

wherein $R^1$, A, Z and $X^1$ are as defined, are reacted with compounds of the formula (V)

$$(R'—S)_2C=N—CN \quad (V)$$

wherein R' represents a lower alkyl group or a benzyl group, or two R' groups may together represent a lower alkylene group having at least 2 carbon atoms and may form a ring together with the adjacent sulfur atoms, in the presence of inert solvents, or (c) in the case where X in the formula (I) represents the group

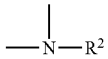

in which $R^2$ represents an acyl group which may be substituted, and for which case in the following formula (VI) $R^2$ is replaced by the symbol $R^5$: Compounds of the formula (Ib)

(Ib)

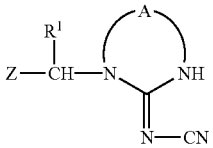

wherein $R^1$, A and Z are as defined above, are reacted with compounds of the formula (VI)

$$R^5—Hal \quad (VI)$$

wherein $R^5$ is as defined above, and Hal represents a halogen atom, in the presence of inert solvents and a base.

The novel heterocyclic compounds of formula (I) exhibit powerful insecticidal properties.

Surprisingly, the novel heterocyclic compounds according to the invention exhibit a substantially greater insecticidal action than those known from the aforesaid prior art, and in particular the the compounds have extremely superior activities as insecticides against stinging and sucking insects typified by hemipterous insects such as aphids, planthoppers and leafhoppers, which have attained resistance to organophosphate and carbamate insecticides as a result of their long-term use.

Among the compounds according to the invention, of the formula (I), preferred compounds are those in which $R^1$ represents a hydrogen atom or a methyl group, A represents an ethylene group which may be substituted by methyl or a trimethylene group which may be substituted by methyl, X represents an oxygen or sulfur atom or the group

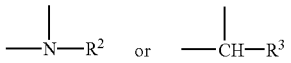

in which $R^2$ represents a hydrogen atom, a $C_1$–$C_4$ alkyl group which may be substituted by a substituent selected from halogens, $C_1$–$C_4$ alkoxy groups, $C_1$–$C_4$ alkylthio groups and cyano, a $C_2$–$C_4$ alkenyl group, a $C_2$–$C_4$ alkynyl group, a pyridylmethyl group which may be substituted by halogen and/or methyl, a benzyl group which may be substituted by halogen and/or methyl, a formyl group, an alkylcarbonyl group having 1 to 2 carbon atoms in the alkyl moiety which may be substituted by halogen, a phenylcarbonyl group which may be substituted by halogen and/or methyl, an alkoxy- or alkylthiocarbonyl group having 1 to 4 carbon atoms in the alkyl moiety, a phenoxycarbonyl group, a $C_1$–$C_4$ alkylsulfonyl group which may be substituted by halogen or a phenylsulfonyl group which may be substituted by methyl, and $R^3$ represents a hydrogen atom, and Z represents a 5- or 6-membered heterocyclic group containing 2 to 3 hetero atoms selected from oxygen, sulfur and nitrogen atoms at least one of which is a nitrogen atom, or a 3-pyridyl group, the heterocyclic group and the 3-pyridyl group being optionally substituted by at least one substituent selected from halogen atoms, alkyl groups having 1 to 4 carbon atoms, alkoxy groups having 1 to 4 carbon atoms, alkylthio groups having 1 to 4 carbon atoms, haloalkyl groups having 1 to 4 carbon atoms, haloalkoxy groups having 1 to 4 carbon atoms, alkylsulfonyl groups having 1 to 4 carbon atoms, a cyano group and a nitro group.

Very particularly preferred compounds of the formula (I) are those in which $R^1$ represents a hydrogen atom, A represents an ethylene or trimethylene group, X represents a sulfur atom or the group —NH, and Z represents a 5- or 6-membered heterocyclic group containing two hetero atoms selected from oxygen, sulfur and nitrogen atoms at least one of which is a nitrogen atom, or a 3-pyridyl group, the heterocyclic group and the 3-pyridyl group being optionally substituted by at least one substituent selected from a fluorine atom, a chlorine atom, a bromine atom, a methyl group, a methoxy group, a methylthio group, a trifluoromethyl group, a trifluoromethoxy group, a methylsulfonyl group, a cyano group and a nitro group.

The 3-pyridyl group in the definition of Z is structurally synonymous with 5-pyridyl.

Specific examples of the compounds of formula (I) in accordance with this invention especially include 1-(2-chloro-5-pyridylmethyl)-2-cyanoiminoimidazolidine,
1-(2-fluoro-5-pyridylmethyl)-2-cyanoiminoimidazolidine,
1-(2-chloro-5-pyridylmethyl)-2-cyanoiminotetrahydropyrimidine,
1-(2-methyl-5-pyridylmethyl)-2-cyanoiminoimidazolidine,
1-(2-chloro-5-thiazolylmethyl)-2-cyanoiminoimidazolidine,
1-(2-chloro-5-thiazolylmethyl)-2-cyanoiminotetrahydropyrimidine,
1-(2-methyl-5-pyrazinylmethyl)-2-cyanoiminoimidazolidine,
1-(2-chloro-5-pyridylmethyl)-2-cyanoiminothiazolidine,
1-(2-chloro-5-pyridylmethyl)-2-cyanoiminotetrahydro-2H-1,2-thiazine
1-(2-chloro-5-thiazolylmethyl)-2-cyanoiminothiazolidine,
1-(2-methyl-5-pyrazinylmethyl)-2-cyanoiminothiazolidine,
1-(2-methyl-5-thiazolylmethyl)-2-cyanoiminothiazolidine, and
1-(1,2,5-thiaziazol-3-yl)-2-cyanoiminothiazolidine.

When in process (a) for the production of the compound of formula (I), 2-cyanoiminothiazolidine and 2-chloro-5-pyridylmethyl chloride are used as the starting materials, the reaction is represented by the following reaction scheme:

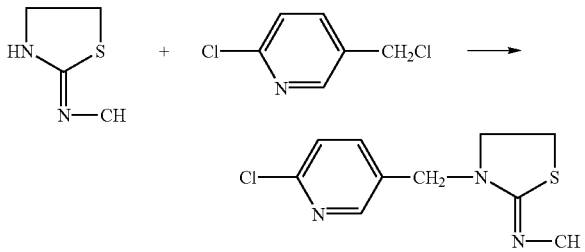

When N-(2-chloro-5-pyridylmethyl)ethylenediamine and dimethylcyanodithioimide carbonate are used as the starting materials in process (b) for the production of the compound of formula (I), the reaction is represented by the following reaction scheme:

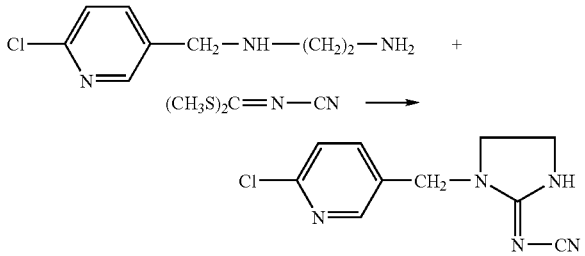

When 1-(2-chloro-5-pyridylmethyl)-2-cyanoiminoimidazolidine and acetyl chloride are used as the starting materials in process (c) for the production of the compound of formula (I), the reaction is represented by the following reaction scheme:

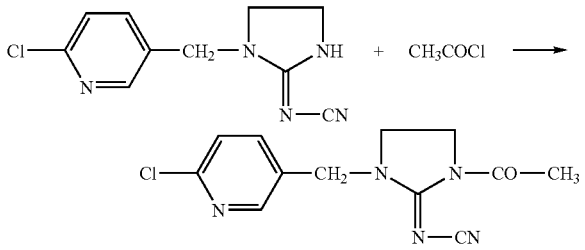

In process (a), the starting compound of the formula (II) means one based on the definitions of A and X. Preferably, A and X are synonymous with the preferred definitions given hereinabove.

The compounds of the formula (II) include known compounds.

2-Cyanoiminoimidazolidine and 2-cyanoiminotetrahydropyridine are described in J. Org. Chem., vol. 38, pages 155–156, and can be easily obtained by the reaction of dimethyl cyanodithioimidocarbonate with ethylenediamine or trimethylenediamine. Likewise, reaction with ethylenediamine or trimethylenediamine N-substituted by substituents other than acyl gives the corresponding 3-substituted-2-cyanoiminoimidazolidine or 3-substituted-2-cyanoiminotetrahydropyrimidine.

Use of aminoalkanols in place of the alkylenediamines can give the corresponding oxazolidines or 1,3-oxazine derivatives (Japanese Laid-Open Patent Publication No. 91064/1973).

2-Cyanoiminothiazolidine is described in Arch. Pharm., vol. 305, pages 731–737. Likewise, the reaction of 2-aminopropanethiol with dimethyl cyanodithioimidocarbonate gives 2-cyanoiminotetrahydro-1,3-thiazine.

2-Cyanoiminopyrrolidine is described in Khim. Farm. Zh., vol. 19, pages 154–158, and can be easily obtained by reacting 2-methoxypyrroline-2 and cyanamide. Similarly, 2-cyanoiminopiperidine is obtained from 2-methoxy-3,4,5,6-tetrahydropyridine with cyanamide.

Likewise, the starting compounds of the formula (III) are those based on the definitions of $R^1$, Z and $M^1$. Preferably, $R^1$, Z are synonymous with the preferred definitions given hereinabove. $M^1$ is preferably a chlorine or bromine atom.

The compounds of the formula (III) are described in Japanese Patent Applications Nos. 18627/1985, 18628/1985, and 106853/1985 filed by the same applicants as the present one. Specific examples include 2-fluoro-5-pyridylmethyl chloride,
2-chloro-5-pyridylmethyl chloride,
2-bromo-5-pyridylmethyl chloride,
2-methyl-5-pyridylmethyl chloride,
2-chloro-5-thiazolylmethyl chloride,
2-methyl-5-pyrazinylmethyl chloride,
2-methyl-5-oxazolylmethyl chloride,
1,2,5-thiaziazol-3-ylmethyl chloride,
3-methyl-5-isoxazolylmethyl chloride, and
2-chloro-5-pyrimidinylmethyl chloride.

In process (b), the starting compounds of the formula (IV) are those based on the definitions of $R^1$, A and Z, and $R^1$, A and Z are synonymous with the preferred definitions given hereinabove.

The compounds of the formula (IV) are described in Japanese Patent Applications Nos. 18627/1985, 18628/1985, 23683/1985, 106853/1985, and 219082/1985. Specific examples include N-(2-chloro-5-pyridylmethyl)-ethylenediamine or trimethylenediamine,
N-(2-fluoro-5-pyridylmethyl)-ethylenediamine or trimethylenediamine,
N-(2-methyl-5-pyridylmethyl)-ethylenediamine or trimethylenediamine,
N-(2-methyl-5-thiazolylmethyl)-ethylenediamine or trimethylenediamine, and
N-(2-methyl-5-pyrazinylmethyl)-ethylenediamine or trimethylenediamine.

Other examples include 2-(2-chloro-5-pyridylmethyl)aminoethanethiol,
3-(2-chloro-5-pyridylmethyl)aminopropanethiol,
2-(2-chloro-5-thiazolylmethyl)aminoethanethiol, and
2-(2-methyl-5-pyrazinylmethyl)aminoethanethiol.

The starting compounds of the formula (V) are described in J. Org. Chem., vol. 32, pages 1566–1572.

In process (c), the starting compounds of the formula (Ib) are included within the compounds of formula (I) in accordance with this invention which can be produced by process (a) or (b).

The starting compounds of the formula (VI) are well known in the field of organic chemistry, and their specific examples include propionyl chloride, acetyl chloride, chloroacetyl chloride, methylsulfonyl chloride, tosyl chloride and methoxycarbonyl chloride.

In the practice of process (a), suitable diluents are used which include all inert organic solvents.

Examples of the diluent include aliphatic, alicyclic and aromatic hydrocarbons (optionally chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acid amides such as dimethylformamide and dimethylacetamide; and sulfones and sulfoxides such as dimethyl sulfoxide and sulfolane.

The reaction of process (a) may be carried out in the presence of a base. Examples of the base are alkali metal hydrides such as sodium hydride and potassium hydride, and hydroxides and carbonates of alkali metals.

Process (a) can be carried out over a broad temperature range, for example between about 0° and about 100° C., preferably between about 10° and about 80° C. Desirably, the reaction is carried out under atmospheric pressure, but it is also possible to operate under reduced pressure.

In the practice of process (a), for example, 1 mole of the compounds of the formula (II) is reacted with 1 to about 1.2 moles, preferably 1 to about 1.1 moles, of the compounds of the formula (III) in an inert solvent such as dimethylformamide in the presence of a base to give the desired compound of general formula (I).

In the practice of process (b), suitable diluents include water and alcohols in addition to the inert organic solvents illustrated for process (a).

Process (b) can be carried out over a broad temperature range, for example between 0° C. and the boiling point of the reaction mixture, preferably between about 0° C. and about 100° C. Preferably, the reaction is carried out under atmospheric pressure, but can also be carried out under elevated or reduced pressure.

In the practice of process (b), for example, 1 mole of the compound of formula (IV) is reacted with 1 to about 1.2 moles, preferably 1 to about 1.1 moles, of the compound of formula (v) in an inert solvent such as an alcohol (e.g., methanol or ethanol) until the generation of mercaptan ceases, to obtain the desired novel compound of general formula (I).

In the practice of process (c), suitable diluents may be the same as those illustrated above for process (a). Process (c) may be carried out in the presence of a base. The same alkali metal hydrides illustrated above for process (a) may be cited as examples of such a base.

Process (c) may be practiced over a broad temperature range, preferably between 0° C. and the boiling point of the mixture, especially between 0° C. and 100° C. Desirably, the reaction is carried out under atmospheric pressure, but may be carried out under elevated or reduced pressure conditions.

The compounds of the formula (I) in accordance with this invention may be present in the form of salts such as inorganic acid salts, sulfonates, organic acid salts and metal salts. Accordingly, the novel heterocyclic compounds of the formula (I) in this invention are meant to denote their salts as well.

The active compounds are well tolerated by plants, have a favourable level of toxicity to warm-blooded animals, and can be used for combating anthropod pests, especially insects which are encountered in agriculture, forestry, in the protection of stored products and of materials, and in the hygiene field. They are active against normally sensitive and resistant species and against all or some stages of development. The above-mentioned pests include:

from the class of the Isopoda, for example Oniscus Asellus, Armadillidium vulgare and Porcellio scaber;

from the class of the Diplopoda, for example Blaniulus guttulatus;

from the class of the Chilopoda, for example Geophilus carpophagus and Scutigera spec.;

from the class of the Symphyla, for example Scutigerella immaculata;

from the order of the Thysanura, for example Lepisma saccharina;

from the order of the Collembola, for example Onychiurus armatus;

from the order of the Orthoptera; for example Blatta orientalis, Periplaneta americana, Leucophaea maderae, Blattella germanica, Acheta domesticus, Gryllotalpa spp., Locusta migratoria migratorioides, Melanoplus differentialis and Schistocerca gregaria;

from the order of the Dermaptera, for example Forficula auricularia;

from the order of the Isoptera, for example Reticulitermes spp.;

from the order of the Anoplura, for example Phylloxera vastatrix, Pemphigus spp., Pediculus humanus corporis, Haematopinus spp. and Linognathus spp.;

from the order of the Mallophaga, for example Trichodectes spp. and Damalinea spp.;

from the order of the Thysanoptera, for example Hercinothrips femoralis and Thrips tabaci, from the order of the Heteroptera, for example Eurygaster spp., Dysdercus intermedius, Piesma guadrata, Cimex lectularius, Rhodnius prolixus and Triatoma spp.;

from the order of the Homoptera, for example Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.;

from the order of the Lepidoptera, for example Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Buccalatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana;

from the order of the Coleoptera, for example Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica;

from the order of the Hymenoptera for example Diprion spp., Hoplocampa spp., Lasius spp., Monomorium pharaonis and Vespa spp., from the order of the Diptera, for example Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa;

In the field of veterinary medicine, the novel compounds of this invention are effective against various noxious animal parasites (endo- and ecto-parasites) such as insects and worms.

Examples of such animal parasites are insects such as Gastrophilus spp., Stomoxys spp., Trichodectes spp., Rhodnius spp., and Ctenocephalides canis.

The active compounds can be converted into the customary formulations, such as solutions, emulsions, suspensions, powders, foams, pastes, granules, aerosols, natural and synthetic materials impregnated with active compounds, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solids carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salt of iron, manganese boron, copper, cobalt, molybdenum and zinc.

The formulations in general contain from 0.1 to 95 per cent by weight of active compound, preferably from 0.5 to 90 per cent by weight of active compound.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates. The following examples illustrate the present invention more specifically. It should be understood however that the invention is in no way limited to these examples alone.

Production Example

EXAMPLE 1

(compound No. 5)

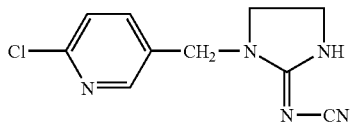

N-(2-chloro-5-pyridylmethyl)ethylenediamine (3.7 g) and dimethyl cyanodithioimidocarbonate (1.3 g) were added to 50 ml of ethanol, and the mixture was gradually heated with stirring and subsequently refluxed for 3 hours. After the reaction, ethanol was distilled off under reduced pressure, whereupon the residue solidified. The solidified residue was pulverized and washed with a mixture of ether and a small amount of ethanol. The amount of the product yielded after drying was 3.5 g. mp. 167°–170° C.

EXAMPLE 2

(compound No. 65)

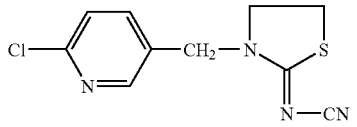

N-(2-chloro-5-pyridylmethyl)cysteamine (2.0 g) and dimethyl cyanodithioimidocarbonate (1.3 g) were added to 50 ml of ethanol. In a stream of nitrogen gas, the mixture was refluxed for 8 hours with stirring. After the reaction, about ⅔ of ethanol was distilled off under reduced pressure. When the residue was left to stand at room temperature, the final product precipitated as crystals. The crystals were collected by filtration, washed with ether and dried. The amount yielded was 2.4 g. mp. 128°–129° C.

EXAMPLE 3

(compound No. 69)

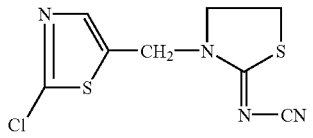

A mixture of 2-cyanoiminothiazolidine (2.5 g), anhydrous potassium carbonate (3.0 g), 2-chloro-5-chloromethylthiazole (3.3 g) and dry acetonitrile was refluxed for 3 hours with good stirring. After the reaction, acetonitrile was distilled off under reduced pressure, and dichloromethane was added to the residue. The mixture was washed with water and a 1% aqueous solution of sodium hydroxide. The dichloromethane layer was dried and concentrated. The precipitate was collected by filtration, and dried. The amount yielded was 3.3 g. mp. 145°–146° C.

EXAMPLE 4

(compound No. 54)

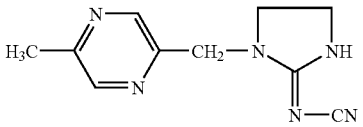

2-Cyanoiminoimidazolidine (2.2 g) was dissolved in 25 ml of dry dimethylformamide, and sodium hydride (1 g) was added little by little at less than 10° C. and the mixture was stirred at 10° C. until the generation of hydrogen ceased. Then, a solution of 2-chloromethyl-5-methylpyrazine (2.8 g) is dimethylformamide (10 ml) was added dropwise at 10° C. After the addition, the mixture was stirred at room temperature for 1 hour. Ice water was added to the mixture, and the pH of the aqueous solution was adjusted to 7. The aqueous layer was extracted with dichloromethane, and the dichloromethane layer was washed with water and dried. After concentrating dichloromethane, the remaining solid was recrystallized from dilute ethanol to give 1.8 g of the final product. mp. 144°–147° C.

EXAMPLE 5

1-(2-Chloro-5-pyridylmethyl)-2-cyanoiminoimidazolidine (2.4 g) was dissolved in 30 ml of dry dimethylformamide, and sodium hydride (0.26 g) was added at 10° C. The mixture was stirred at room temperature until the generation of hydrogen ceased. Then, benzoyl chloride (1.4 g) was added, and the mixture was stirred at 40° C. for 30 minutes, and poured into ice water. The aqueous layer was extracted with dichloromethane. The dichloromethane layer was washed with water, and dichloromethane was concentrated. The residue was purified by silica gel column chromatography to give the final product. The amount yielded was 1.3 g. mp. 158°–161° C.

The compounds shown in Table 1 can be prepared in the same way as exemplified in Examples 1 to 5. Table 1 also discloses the compounds obtained in Examples 1 to 5.

(compound No. 89)

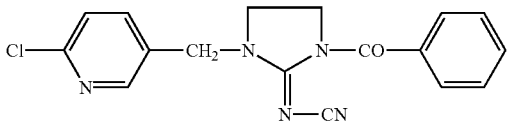

TABLE 1

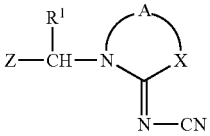

| Compound No. | Z—CH(R′)— | A | X | |
|---|---|---|---|---|
| 1 | 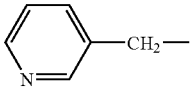 | —$CH_2CH_2$— | NH | |
| 2 | 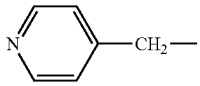 | —$CH_2CH_2$— | NH | mp. 191~193° C. |
| 3 | 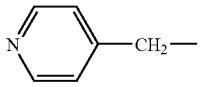 | —$(CH_2)_3$— | NH | mp. 214~216° C. |
| 4 | 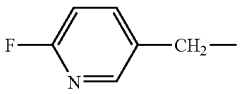 | —$CH_2CH_2$— | NH | mp. 154~157° C. |
| 5 | 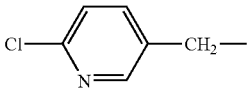 | —$CH_2CH_2$— | NH | mp. 167~170° C. |
| 6 | 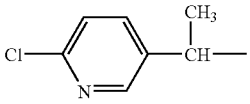 | —$CH_2CH_2$— | NH | |
| 7 | 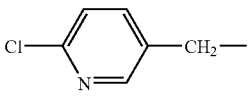 | —$CH_2CH(CH_3)$— | NH | mp. 155~160° C. |

TABLE 1-continued
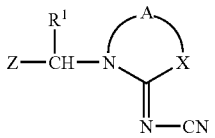
| Compound No. | Z—CH(R′)— | A | X | |
|---|---|---|---|---|
| 8 | 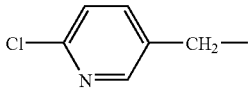 | —$(CH_2)_3$— | NH | mp. 166~167.5° C. |
| 9 | 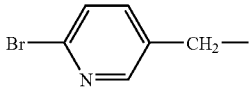 | —$CH_2CH_2$— | NH | |
| 10 | 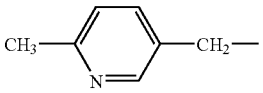 | —$CH_2CH_2$— | NH | |
| 11 | 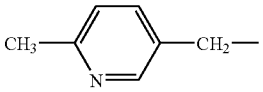 | —$(CH_2)_3$— | NH | mp. 184~188° C. |
| 12 | 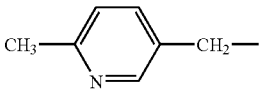 | —$CH_2CH(CH_3)CH_2$— | NH | |
| 13 | 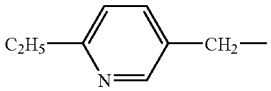 | —$CH_2CH_2$— | NH | |
| 14 | 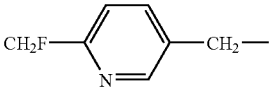 | —$CH_2CH_2$— | NH | |
| 15 | 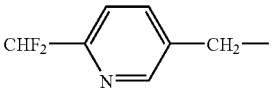 | —$CH_2CH_2$— | NH | |
| 16 | 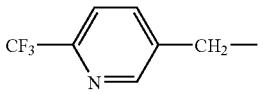 | —$CH_2CH_2$— | NH | |
| 17 | 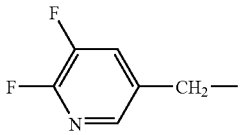 | —$CH_2CH_2$— | NH | |
| 18 | 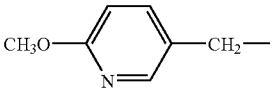 | —$CH_2CH_2$— | NH | |
| 19 | 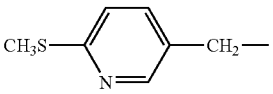 | —$(CH_2)_3$— | NH | |

TABLE 1-continued
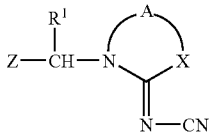
| Compound No. | Z—CH(R′)— | A | X | |
|---|---|---|---|---|
| 20 | 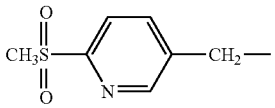 | —$CH_2CH_2$— | NH | |
| 21 | 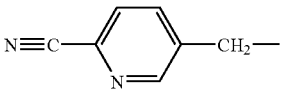 | —$CH_2CH_2$— | NH | |
| 22 | 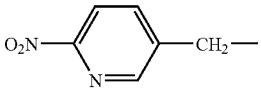 | —$CH_2CH_2$— | NH | |
| 23 | 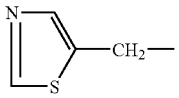 | —$(CH_2)_3$— | NH | |
| 24 | 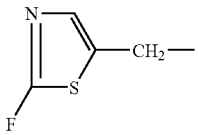 | —$(CH_2)_3$— | NH | |
| 25 | 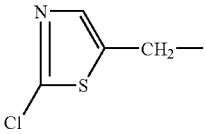 | —$CH_2CH_2$— | NH | mp. 161~162° C. |
| 26 | 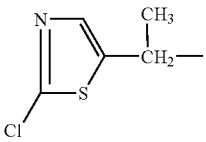 | —$CH_2CH_2$— | NH | |
| 27 | 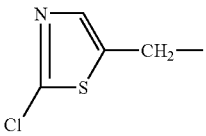 | —$(CH_2)_3$— | NH | mp. 182~185° C. |
| 28 | 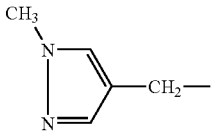 | —$(CH_2)_3$— | NH | |
| 29 | 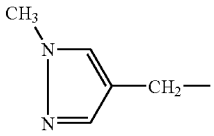 | 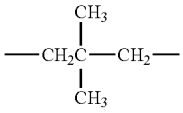 | NH | mp. 224~227° C. |

TABLE 1-continued
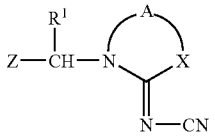
| Compound No. | Z—CH(R′)— | A | X | |
|---|---|---|---|---|
| 30 | 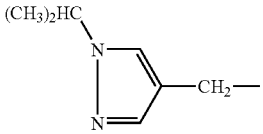 | —$CH_2CH_2$— | NH | |
| 31 | 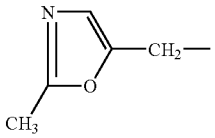 | —$CH_2CH_2$— | NH | |
| 32 | 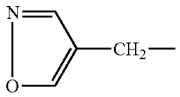 | —$CH_2CH_2$— | NH | |
| 33 | 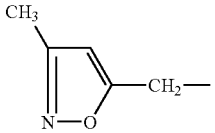 | —$(CH_2)_3$— | NH | mp. 145~148° C. |
| 34 | 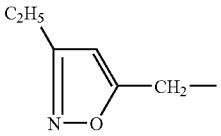 | —$CH_2CH_2$— | NH | mp. 129~131° C. |
| 35 | 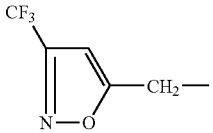 | —$(CH_2)_3$— | NH | |
| 36 | 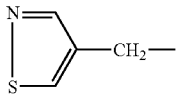 | —$CH_2CH_2$— | NH | |
| 37 | 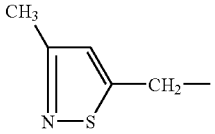 | —$(CH_2)_3$— | NH | |
| 38 | 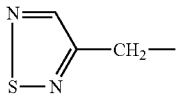 | —$CH_2CH_2$— | NH | |
| 39 | 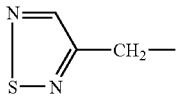 | —$(CH_2)_3$— | NH | mp. 137~140° C. |

TABLE 1-continued
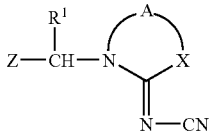
| Compound No. | Z—CH(R′)— | A | X | |
|---|---|---|---|---|
| 40 | 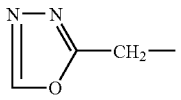 | —$(CH_2)_3$— | NH | |
| 41 | 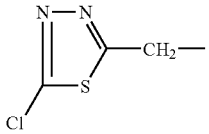 | —$(CH_2)_3$— | NH | |
| 42 | 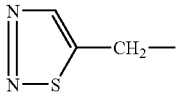 | —$CH_2CH_2$— | NH | |
| 43 | 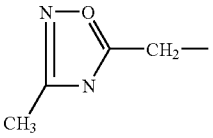 | —$(CH_2)_3$— | NH | |
| 44 | 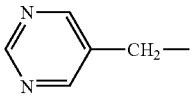 | —$CH_2CH_2$— | NH | |
| 45 | 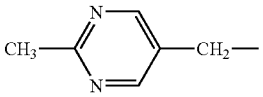 | —$CH_2CH_2$— | NH | |
| 46 | 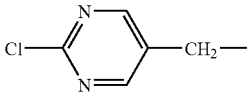 | —$CH_2CH_2$— | NH | |
| 47 | 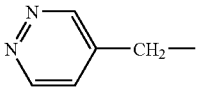 | —$CH_2CH_2$— | NH | |
| 48 | 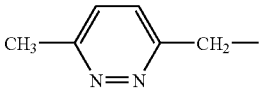 | —$(CH_2)_3$— | NH | |
| 49 | 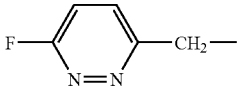 | —$CH_2CH_2$— | NH | |
| 50 | 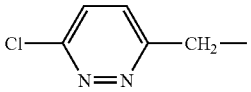 | —$CH_2CH_2$— | NH | |
| 51 | 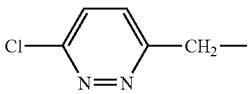 | —$(CH_2)_3$— | NH | mp. 185~188° C. |

TABLE 1-continued
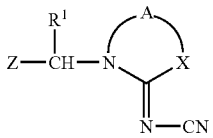
| Compound No. | Z—CH(R′)— | A | X | |
|---|---|---|---|---|
| 52 | 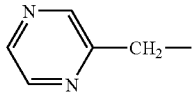 | —$CH_2CH_2$— | NH | |
| 53 | 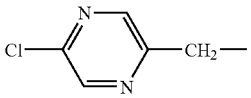 | —$CH_2CH_2$— | NH | |
| 54 | 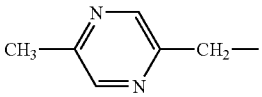 | —$CH_2CH_2$— | NH | mp. 144~147° C. |
| 55 | 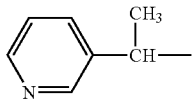 | —$CH_2CH_2$— | N—CHO | |
| 56 | 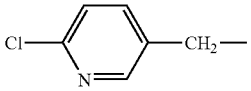 | —$CH_2CH_2$— | N—$COCH_3$ | $n_D^{20}$ 1.5895 |
| 57 | 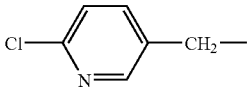 | —$CH_2CH_2$— | 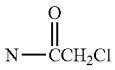 | mp. 53~55° C. |
| 58 | 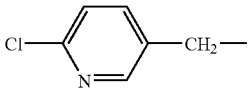 | —$CH_2CH_2$— | N—$COC(CH_3)_3$ | |
| 59 | 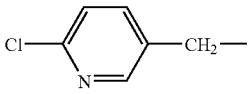 | —$CH_2CH_2$— | 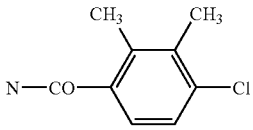 | |
| 60 | 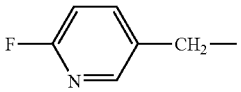 | —$(CH_2)_3$— | 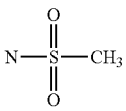 | |
| 61 | 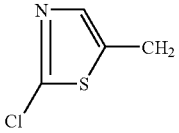 | —$(CH_2)_3$— | N—$COOC_2H_3$ | |
| 62 | 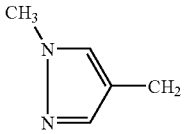 | —$CH_2CH_2$— | 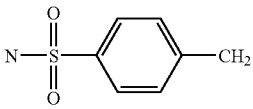 | |

TABLE 1-continued
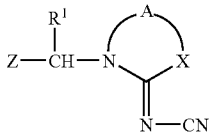
| Compound No. | Z—CH(R′)— | A | X | |
|---|---|---|---|---|
| 63 | 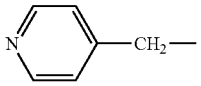 | —$CH_2CH_2$— | S | |
| 64 | 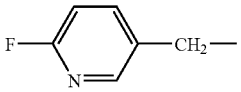 | —$CH_2CH_2$— | S | mp. 117~120° C. |
| 65 | 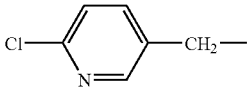 | —$CH_2CH_2$— | S | mp. 128~129° C. |
| 66 | 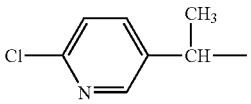 | —$CH_2CH_2$— | S | |
| 67 | 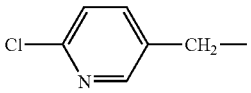 | —$(CH_2)_3$— | S | mp. 124~125° C. |
| 68 | 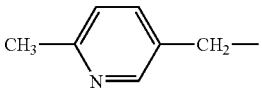 | —$CH_2CH_2$— | S | |
| 69 | 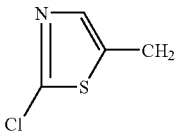 | —$CH_2CH_2$— | S | mp. 145~146° C. |
| 70 | 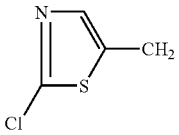 | —$(CH_2)_3$— | S | |
| 71 | 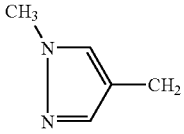 | —$(CH_2)_3$— | S | |
| 72 | 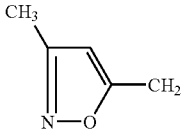 | —$(CH_2)_3$— | S | |
| 73 | 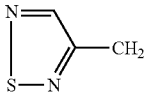 | —$CH_2CH_2$— | S | mp. 153~157° C. |

TABLE 1-continued
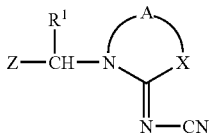
| Compound No. | Z—CH(R′)— | A | X | |
|---|---|---|---|---|
| 74 | 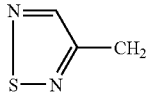 | —$(CH_2)_3$— | S | |
| 75 | 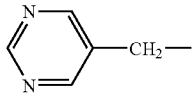 | —$CH_2CH_2$— | S | |
| 76 | 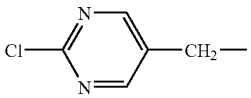 | —$CH_2CH_2$— | S | |
| 77 | 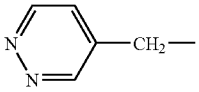 | —$CH_2CH_2$— | S | |
| 78 | 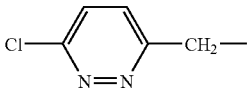 | —$(CH_2)_3$— | S | |
| 79 | 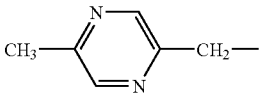 | —$CH_2CH_2$— | S | mp. 132~135° C. |
| 80 | 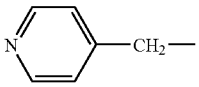 | —$CH_2CH_2$— | O | |
| 81 | 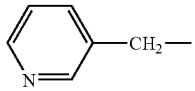 | —$CH_2CH_2$— | O | |
| 82 | 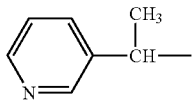 | —$CH_2CH_2$— | O | |
| 83 | 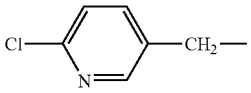 | —$CH_2CH_2$— | O | mp. 113~114° C. |
| 84 | 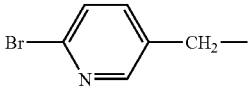 | —$(CH_2)_3$— | O | |
| 85 | 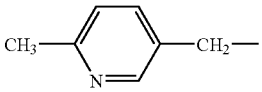 | —$CH_2CH_2$— | O | |

TABLE 1-continued
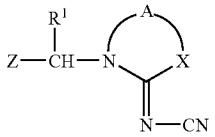
| Compound No. | Z—CH(R′)— | A | X | |
|---|---|---|---|---|
| 86 | 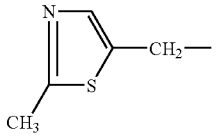 | —$CH_2CH_2$— | O | |
| 87 | 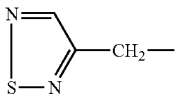 | —$(CH_2)_3$— | O | |
| 88 | 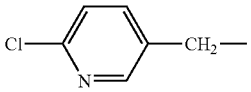 | —$CH_2CH_2$— | N—$COCCl_3$ | |
| 89 | 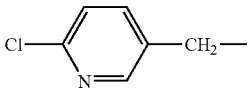 | —$CH_2CH_2$— | 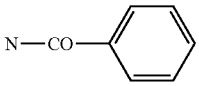 | mp. 158~161° C. |
| 90 | 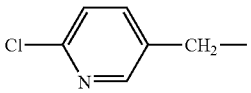 | —$CH_2CH_2$— | N—$COOCH_3$ | |
| 91 | 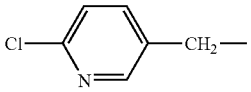 | —$CH_2CH_2$— | 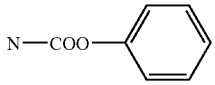 | |
| 92 | 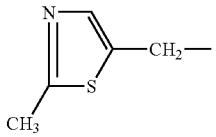 | —$CH_2CH_2$— | N—$COCH_3$ | |
| 93 | 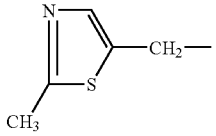 | —$CH_2CH_2$— | N—$COOCH_3$ | |
| 94 | 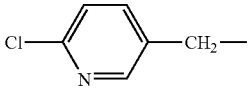 | —$(CH_2)_3$— | N—$COSC_2H_3$ | |
| 95 | 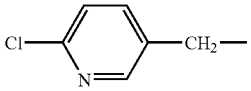 | —$(CH_2)_3$— | 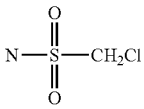 | |
| 96 | 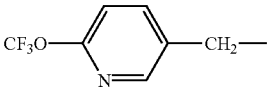 | —$CH_2CH_2$— | N—$COC_2H_3$ | |

TABLE 1-continued
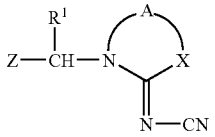
| Compound No. | Z—CH(R′)— | A | X | |
|---|---|---|---|---|
| 97 | 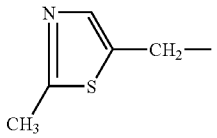 | —$CH_2CH_2$— | S | mp. 138~140° C. |
| 98 | 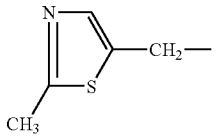 | —$(CH_2)_3$— | S | |
| 99 | 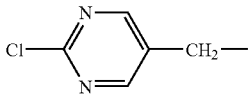 | —$CH_2CH_2$— | O | |
| 100 | 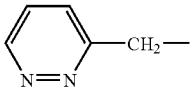 | —$CH_2CH_2$— | O | |
| 101 | 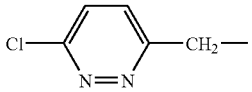 | —$CH_2CH_2$— | O | |
| 102 | 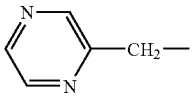 | —$(CH_2)_3$— | O | |
| 103 | 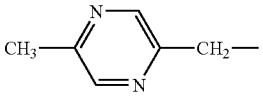 | —$CH_2CH_2$— | O | mp. 130~134° C. |
| 104 | 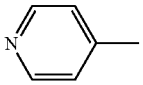 | —$CH_2CH_2$— | $CH_2$ | |
| 105 | 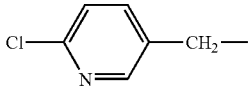 | —$CH_2CH_2$— | $CH_2$ | |
| 106 | 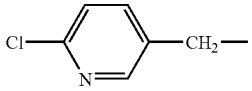 | —$CH_2CH_2$— | CH—$CH_3$ | |
| 107 | 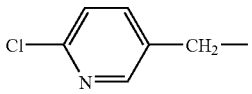 | —$(CH_2)_3$— | $CH_2$ | mp. 74~76° C. |
| 108 | 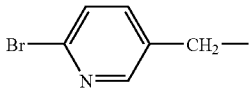 | —$CH_2CH_2$— | $CH_2$ | |

TABLE 1-continued
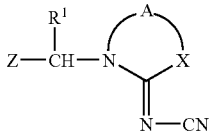
| Compound No. | Z—CH(R′)— | A | X | |
|---|---|---|---|---|
| 109 | 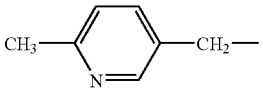 | —$CH_2CH_2$— | $CH_2$ | |
| 110 | 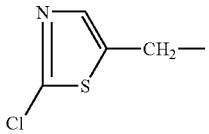 | —$CH_2CH_2$— | $CH_2$ | |
| 111 | 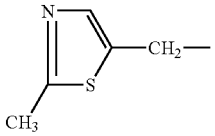 | —$(CH_2)_3$— | $CH_2$ | mp. 122~125° C. |
| 112 | 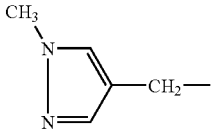 | —$(CH_2)_3$— | $CH_2$ | |
| 113 | 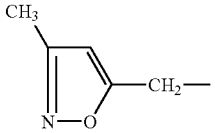 | —$CH_2CH_2$— | $CH_2$ | |
| 114 | 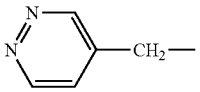 | —$CH_2CH_2$— | O | |
| 115 | 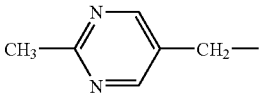 | —$CH_2CH_2$— | O | |
| 116 | 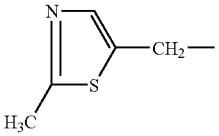 | —$(CH_2)_3$— | NH | mp. 185~190° C. |
| 117 | 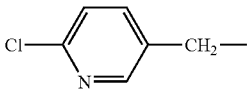 | —$CH_2CH_2$— | N—$CH_3$ | mp. 101~103° C. |
| 118 | 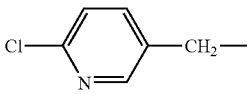 | —$CH_2CH_2$— | N—$CH_2CN$ | $n_D^{20}$ 1.6015 |
| 119 | 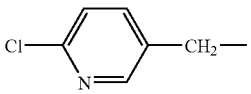 | —$CH_2CH_2$— | N—$CH_2CF_3$ | |

TABLE 1-continued
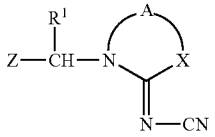
| Compound No. | Z—CH(R′)— | A | X | |
|---|---|---|---|---|
| 120 | 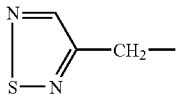 | —$(CH_2)_3$— | N—$CH_2CH_2OCH_3$ | |
| 121 | 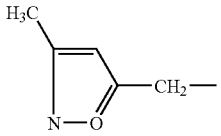 | —$CH_2CH_2$— | N—$CH_2CH_2SC_2H_3$ | |
| 122 | 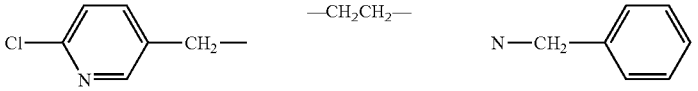 | —$CH_2CH_2$— | | $n_D^{20}$ 1.6145 |
| 123 | 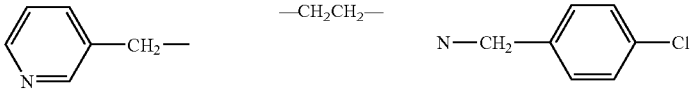 | —$CH_2CH_2$— | | |
| 124 | 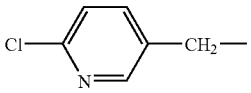 | —$CH_2CH_2$— | N—$CH_2CH{=}CH_2$ | |
| 125 | 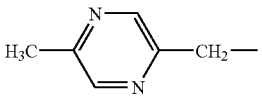 | —$CH_2CH_2$— | N—$CH_2C{\equiv}CH$ | |
| 126 | 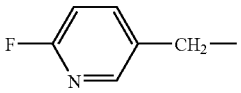 | —$CH_2CH_2$— | N—$CH_2CH_2CN$ | |
| 127 | 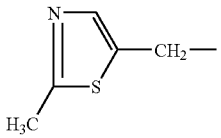 | —$(CH_2)_3$— | S | mp. 141~145° C. |
| 128 | 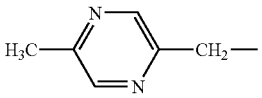 | —$CH_2CH_2$— | $CH_2$ | mp. 85~90° C. |
| 129 | 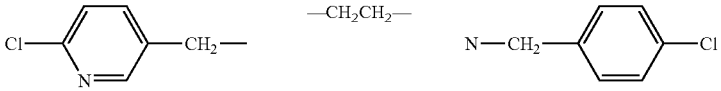 | —$CH_2CH_2$— | | mp. 161~163° C. |
| 130 | 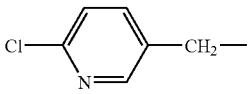 | —$CH_2CH_2$— | N—$COOC_2H_3$ | $n_D^{20}$ 1.5880 |

TABLE 1-continued

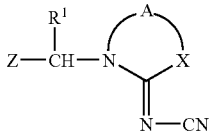

| Compound No. | Z—CH(R′)— | A | X | |
|---|---|---|---|---|
| 131 | 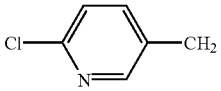 | —$CH_2CH(CH_3)$— | 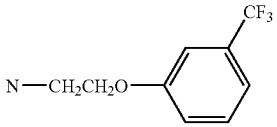 | mp. 82~85° C. |
| 132 | 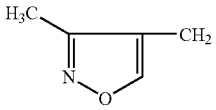 | —$(CH_2)_3$— | N—$CH_2C{\equiv}CH$ | $n_D^{20}$ 1.5667 |
| 133 | 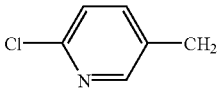 | —$CH_2CH_2$— | 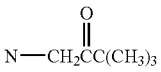 | $n_D^{20}$ 1.5446 |
| 134 | 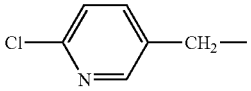 | —$CH_2CH(CH_3)$— | O | mp. 119~121° C. |

Use Examples

Comparison compounds of the closest state of the art:

W-1

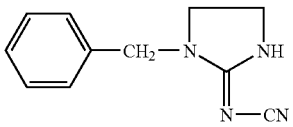

(described in Japanese Laid-Open Patent Publication No. 91064)

W-2

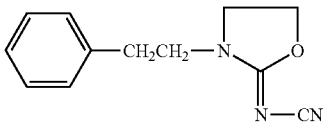

(described in the above-cited patent document)

Q-1

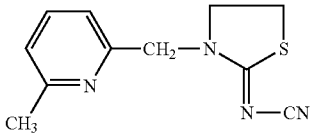

(described in Japanese Laid-Open Patent Publication No. 196877/1984)

EXAMPLE 6 (biological test)

Test on organophosphate-resistant green rice leafhoppers (Nephotettix cincticeps)

Preparation of a test chemical

Solvent: 3 parts by weight of xylene

Emulsifier: 1 part by weight of polyoxyethylene alkylphenyl ether

To prepare a preparation of a suitable active compound, 1 part by weight of the active compound was mixed with the above amount of the solvent containing the above amount of the emulsifier, and the mixture was diluted with water to a predetermined concentration.

Testing method

A water dilution of each of the active compounds in a predetermined concentration prepared as above was sprayed onto rice plants, about 10 cm tall, grown in pots having a diameter of 12 cm at a rate of 10 ml per pot. The sprayed chemical was dried, and a wire net having a diameter of 7 cm and a height of 14 cm was put over each of the pots, and 30 female imagoes of rice leafhopper of a strain having resistance to organophosphate chemicals were released into the net. The pots were placed in a constant-temperature chamber. Two days later, the number of dead insects was examined, and the kill ratio was calculated.

Compared with comparison compounds W-1, W-2 and Q2 for example the following compounds according to the invention exhibited a considerably better efficacy: Compound Nos. 4, 5, 8,9, 25, 27, 54, 65, 67, 69, 79.

EXAMPLE 7 (biological test)

Test on planthoppers

Testing method

A water dilution of each of the active compounds in a predetermined concentration prepared as in the preceding example was sprayed onto rice plants, 10 cm tall, grown in pots having a diameter of 12 cm at a rate of 10 ml per pot. The sprayed chemical was dried, and a wire net having a diameter of 7 cm and a height of 14 cm was put over each of the pots, and 30 female imagoes of brown planthopper (Nilaparvata lugens) of a strain having resistance to organophosphate chemicals were released into the net and the pots were placed in a constant temperature chamber. Two days later, the number of dead insects was examined, and the kill ratio was calculated.

In the same way as above, the kill ratio on white-backed planthopper (Sogatella furcifera) and organophosphate-resistant smaller brown planthopper (Laodelphax striatellus) was calculated.

Compared with comparison compounds W-1, W-2 and Q-1 for example the following compounds according to the invention exhibited a considerably better efficacy against brown planthoppers, brown smaller planthoppers and white-backed planthoppers: Compounds No. 4, 5, 8, 9, 25, 27, 65, 67.

EXAMPLE 8 (biological test)

Test on green peach aphids (Myzus persicae) having resistance to organophosphate and carbamate chemicals Testing method Bred green peach aphids having resistance to organophosphates and carbamates were inoculated on eggplant (black elongate variety) seedlings, about 20 cm tall, grown in unglazed pots having a diameter of 15 cm at a rate of about 200 per seedling. One day after the inoculation, a water dilution of each of the active compounds in a predetermined concentration prepared as in Example 6 was sprayed in sufficient amounts by means of a spray gun. After the spraying, the pots were left to stand in a greenhouse kept at 28° C. Twenty-four hours after the spraying, the kill ratio was calculated. The above test was carried out through two replicates.

Compared with comparison compounds W-1, W-2 and Q-2 for example the following compounds according to the invention exhibited a considerably better efficacy against Myzus persicae: Compounds No. 4, 5, 25, 27, 65, 67, 69.

The biological tests shown in Examples 6, 7 and 8 are only typical examples of the insecticidal use of the compounds of this invention. The compounds of this invention shown herein are typical examples, and the utility of the invention is not to be limited to these examples alone.

It will be understood that the specification and examples are illustrative but not limitative of the present invention and that other embodiments within the spirit and scope of the invention will suggest themselves to those skilled in the art.

We claim:

[1. A heterocyclic compound of the formula

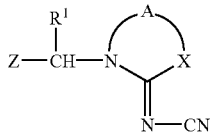

wherein $R^1$ represents a hydrogen atom or a methyl group,

A represents an ethylene group which may be substituted by methyl,

X represents an oxygen or sulfur atom or the group

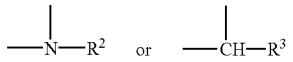

in which $R^2$ represents a hydrogen atom, a $C_1$–$C_4$ alkyl group which may be substituted by a substituent selected from halogens, $C_1$–$C_4$ alkoxy groups, $C_1$–$C_4$ alkylthio groups and cyano, a $C_2$–$C_4$ alkenyl group, a $C_2$–$C_4$ alkynyl group, a pyridylmethyl group, which may be substituted by halogen and/or methyl, a benzyl group which may be substituted by halogen and/or methyl, a formyl group, an alkylcarbonyl group having 1 to 2 carbon atoms in the alkyl moiety which may be substituted by halogen, a phenylcarbonyl group which may be substituted by halogen and/or methyl, an alkoxy or alkylthiocarbonyl group having 1 to 4 carbon atoms in the alkyl moiety, a phenoxycarbonyl group, a $C_1$–$C_4$ alkylsulfonyl group which may be substituted by halogen or a phenylsulfonyl group which may be substituted by methyl, $R^3$ represents a hydrogen atom or a $C_1$–$C_7$ alkyl group, and Z represents a 3-pyridyl group or a 4-pyridyl group optionally substituted by at least one substituent selected from halogen atoms, alkyl groups having 1 to 4 carbon atoms, alkoxy groups having 1 to 4 carbon atoms, alkylthio groups having 1 to 4 carbon atoms, haloalkyl groups having 1 to 4 carbon atoms, haloalkoxy groups having 1 to 4 carbon atoms, alkylsulfonyl groups having 1 to 4 carbon atoms, a cyano group and a nitro group.]

[2. A compound according to claim 1, wherein $R^1$ represents a hydrogen atom,

A represents an ethylene group,

X represents a sulfur atom or the group

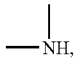

and

Z represents a 3-pyridyl group or a 4-pyridyl gr optionally substituted by at least one substituent selected from a flourine atom, a chlorine atom, a bromine atom, a methyl group, a methoxy group, a methylthio group, a trifluoromethyl group, a trifluoromethoxy group, a methylsulfonyl group, a cyano group and a nitro group.]

[3. A compound according to claim 1, wherein such compound is 1-(2-chloro-5-pyridylmethyl)-2-cyanoiminoimidazolidine of the formula

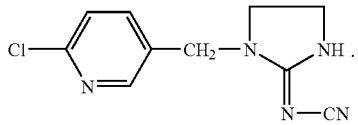

]

[4. A compound according to claim 1, wherein such compound is 1-(2-fluoro-5-pyridylmethyl)-2-cyanoiminoimidazolidine of the formula

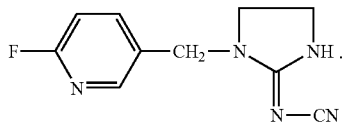

]

[5. A compound according to claim 1, wherein such compound is 1-(2-methyl-5-pyridylmethyl)-2-cyanoiminoimidazolidine of the formula

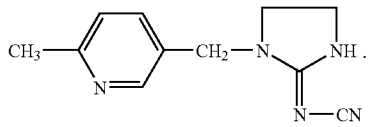

]

[6. A compound according to claim 1, wherein such compound is 1-(2-chloro-5-pyridylmethyl)-2-cyanoiminothiazolidine of the formula

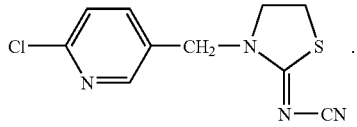

]

[7. An insecticidal composition comprising an insecticidally effective amount of a compound according to claim 1 and a diluent.]

[8. A method of combating insects which comprises applying to such insects or to an insect habitat an insecticidally effective amount of a compound according to claim 1.]

9. [The method according to claim 8, wherein such compound is] *A method of combating insects which comprises applying to such insects or to an insect habitat an insecticidally effective amount of*

[1-(2-chloro-5-pyridylmethyl)-2-cyanoiminoimidazolidine,
1-(2-fluoro-5-pyridylmethyl)-2-cyanoiminoimidazolidine,]
1-(2-chloro-5-pyridylmethyl)-2-cyanoiminotetrahydropyrimidine[,] *or*
[1-(2-methyl-5-pyridylmethyl)-2-cyanoiminoimidazolidine,
1-(2-chloro-5-thiazolylmethyl)-2-cyanoiminoimidazolidine,]
1-(2-chloro-5-thiazolylmethyl)-2-cyanoiminotetrahydropyrimidine[,]
[1-(2-methyl-5-pyrazinylmethyl)-2-cyanoiminoimidazolidine,
1-(2-chloro-5-pyridylmethyl)-2-cyanoiminothiazolidine,
1-(2-chloro-5-pyridylmethyl)-2-cyanoiminotetrahydro-2H-1,3-thiazine,
1-(2-chloro-5-thiazolylmethyl)-2-cyanoiminothiazolidine,
1-(2-methyl-5-pyrazinylmethyl)-2-cyanoiminothiazolidine,
1-(2-methyl-5-thiazolylmethyl)-2-cyanoiminothiazolidine, or
1-(1,2,5-thiaziazol-3-ylmethyl)-2-cyanoiminothiazolidine].

* * * * *